(12) United States Patent
Johnson

(10) Patent No.: US 12,046,325 B2
(45) Date of Patent: Jul. 23, 2024

(54) SYSTEM AND METHOD FOR SEQUENCE IDENTIFICATION IN REASSEMBLY VARIANT CALLING

(71) Applicant: Seven Bridges Genomics Inc., Charlestown, MA (US)

(72) Inventor: Ivan Johnson, Newton Upper Falls, MA (US)

(73) Assignee: Seven Bridges Genomics Inc., Charlestown, MA (US)

( * ) Notice: Subject to any disclaimer, the term of this patent is extended or adjusted under 35 U.S.C. 154(b) by 968 days.

(21) Appl. No.: 16/276,070

(22) Filed: Feb. 14, 2019

(65) Prior Publication Data
US 2019/0267110 A1    Aug. 29, 2019

Related U.S. Application Data

(60) Provisional application No. 62/630,347, filed on Feb. 14, 2018.

(51) Int. Cl.
G16B 20/20  (2019.01)
C12Q 1/68   (2018.01)
(Continued)

(52) U.S. Cl.
CPC .............. *G16B 20/20* (2019.02); *C12Q 1/68* (2013.01); *G16B 30/10* (2019.02); *G16B 30/20* (2019.02)

(58) Field of Classification Search
CPC ........ G16B 20/20; G16B 30/10; G16B 30/20; C12Q 1/68
(Continued)

(56) References Cited

U.S. PATENT DOCUMENTS 5,511,158 A    4/1996  Sims
5,701,256 A    12/1997 Marr et al.
(Continued)

FOREIGN PATENT DOCUMENTS

WO    2012096579 A3    7/2012
WO    2012098515 A1    7/2012
(Continued)

OTHER PUBLICATIONS

EJ Fox, KS Reid-Bayliss, MJ Emond, LA Loeb: "Accuracy of Next Generation Sequencing Platforms", Next Gener Seq Appl. 2014. (Year: 2014).*
(Continued)

*Primary Examiner* — Larry D Riggs, II
*Assistant Examiner* — Guozhen Liu
(74) *Attorney, Agent, or Firm* — Wolf, Greenfield & Sacks, P.C.

(57) ABSTRACT

In one embodiment, a method for identifying candidate sequences for genotyping a genomic sample comprises obtaining a plurality of sequence reads mapping to a genomic region of interest. The plurality of sequence reads are assembled into a directed acyclic graph (DAG) comprising a plurality of branch sites representing variation present in the set of sequence reads, each branch site comprising two or more branches. A path through the DAG comprises a set of successive branches over two or more branch sites and represents a possible candidate sequence of the genomic sample. One or more paths through the DAG are ranked by calculating scores for one or more branch sites, wherein the calculated score comprises a number of sequence reads that span multiple branch sites in a given path. At least one path is selected as a candidate sequence based at least in part on its rank.

17 Claims, 8 Drawing Sheets

Specification includes a Sequence Listing.

(51) Int. Cl.
   *G16B 30/00* (2019.01)
   *G16B 30/10* (2019.01)
   *G16B 30/20* (2019.01)
(58) Field of Classification Search
   USPC .......................................................... 702/20
   See application file for complete search history.

(56) References Cited

U.S. PATENT DOCUMENTS

| | | | |
|---|---|---|---|
| 6,054,278 | A | 4/2000 | Dodge et al. |
| 6,223,128 | B1 | 4/2001 | Allex et al. |
| 7,577,554 | B2 | 8/2009 | Lystad et al. |
| 7,580,918 | B2 | 8/2009 | Chang et al. |
| 7,809,509 | B2 | 10/2010 | Milosavljevic |
| 7,885,840 | B2 | 2/2011 | Sadiq et al. |
| 7,917,302 | B2 | 3/2011 | Rognes |
| 8,209,130 | B1 | 6/2012 | Kennedy et al. |
| 8,340,914 | B2 | 12/2012 | Gatewood et al. |
| 8,370,079 | B2 | 2/2013 | Sorenson et al. |
| 8,639,847 | B2 | 1/2014 | Blaszczak et al. |
| 9,063,914 | B2 | 6/2015 | Kural et al. |
| 9,092,402 | B2 | 7/2015 | Kural et al. |
| 9,116,866 | B2 | 8/2015 | Kural |
| 9,390,226 | B2 | 7/2016 | Kural |
| 9,817,944 | B2 | 11/2017 | Kural |
| 2004/0023209 | A1 | 2/2004 | Jonasson |
| 2005/0089906 | A1 | 4/2005 | Furuta et al. |
| 2006/0292611 | A1 | 12/2006 | Berka et al. |
| 2007/0166707 | A1 | 7/2007 | Schadt et al. |
| 2008/0077607 | A1 | 3/2008 | Gatawood et al. |
| 2008/0294403 | A1 | 11/2008 | Zhu et al. |
| 2009/0119313 | A1 | 5/2009 | Pearce |
| 2009/0164135 | A1 | 6/2009 | Brodzik et al. |
| 2009/0300781 | A1 | 12/2009 | Bancroft et al. |
| 2010/0041048 | A1 | 2/2010 | Diehl et al. |
| 2010/0169026 | A1 | 7/2010 | Sorenson et al. |
| 2011/0004413 | A1 | 1/2011 | Carnevali et al. |
| 2011/0098193 | A1 | 4/2011 | Kingsmore et al. |
| 2012/0041727 | A1 | 2/2012 | Mishra et al. |
| 2012/0045771 | A1 | 2/2012 | Beier et al. |
| 2012/0239706 | A1 | 9/2012 | Steinfadt |
| 2012/0330566 | A1 | 12/2012 | Chaisson |
| 2013/0059738 | A1 | 3/2013 | Leamon et al. |
| 2013/0059740 | A1 | 3/2013 | Drmanac et al. |
| 2013/0073214 | A1 | 3/2013 | Hyland et al. |
| 2013/0124100 | A1 | 5/2013 | Drmanac et al. |
| 2013/0289099 | A1 | 10/2013 | Goff et al. |
| 2013/0311106 | A1 | 11/2013 | White et al. |
| 2013/0332081 | A1* | 12/2013 | Reese .................... G16B 20/00 702/19 |
| 2014/0025312 | A1 | 1/2014 | Chin et al. |
| 2014/0051588 | A9 | 2/2014 | Drmanac et al. |
| 2014/0066317 | A1 | 3/2014 | Talasaz |
| 2014/0136120 | A1 | 5/2014 | Colwell et al. |
| 2014/0200147 | A1 | 7/2014 | Bartha et al. |
| 2014/0278590 | A1 | 9/2014 | Abbassi et al. |
| 2014/0280360 | A1 | 9/2014 | Webber et al. |
| 2014/0323320 | A1 | 10/2014 | Jia et al. |
| 2015/0056613 | A1 | 2/2015 | Kural |
| 2015/0057946 | A1 | 2/2015 | Kural |
| 2015/0094212 | A1 | 4/2015 | Gottimukkala et al. |
| 2015/0110754 | A1 | 4/2015 | Bai et al. |
| 2015/0112602 | A1 | 4/2015 | Kural et al. |
| 2015/0112658 | A1 | 4/2015 | Kural et al. |
| 2015/0197815 | A1 | 7/2015 | Kural |
| 2015/0199472 | A1 | 7/2015 | Kural |
| 2015/0199473 | A1 | 7/2015 | Kural |
| 2015/0199474 | A1 | 7/2015 | Kural |
| 2015/0199475 | A1 | 7/2015 | Kural |
| 2015/0227685 | A1 | 8/2015 | Kural |
| 2015/0293994 | A1 | 10/2015 | Kelly |
| 2015/0302145 | A1 | 10/2015 | Kural et al. |
| 2015/0310167 | A1 | 10/2015 | Kural et al. |
| 2015/0344970 | A1 | 12/2015 | Vogelstein et al. |
| 2015/0347678 | A1 | 12/2015 | Kural |
| 2015/0356147 | A1 | 12/2015 | Mishra et al. |
| 2016/0259880 | A1* | 9/2016 | Semenyuk ............. G16B 15/00 |
| 2016/0306921 | A1 | 10/2016 | Kural |
| 2016/0364523 | A1 | 12/2016 | Locke et al. |
| 2017/0058320 | A1 | 3/2017 | Locke et al. |
| 2017/0058341 | A1 | 3/2017 | Locke et al. |
| 2017/0058365 | A1 | 3/2017 | Locke et al. |
| 2017/0198351 | A1 | 7/2017 | Lee et al. |
| 2017/0199959 | A1 | 7/2017 | Locke |
| 2017/0199960 | A1 | 7/2017 | Ghose et al. |
| 2017/0242958 | A1 | 8/2017 | Brown |

FOREIGN PATENT DOCUMENTS

| | | | |
|---|---|---|---|
| WO | 2012142531 | A2 | 10/2012 |
| WO | 2015027050 | A1 | 2/2015 |
| WO | 2015048753 | A1 | 4/2015 |
| WO | 2015058093 | A1 | 4/2015 |
| WO | 2015058095 | A1 | 4/2015 |
| WO | 2015058097 | A1 | 4/2015 |
| WO | 2015058120 | A1 | 4/2015 |
| WO | 2015061099 | A1 | 4/2015 |
| WO | 2015061103 | A1 | 4/2015 |
| WO | 2015105963 | A1 | 7/2015 |
| WO | 2015123269 | A1 | 8/2015 |
| WO | 2016141294 | A1 | 9/2016 |
| WO | 2016201215 | A1 | 12/2016 |
| WO | 2017120128 | A1 | 7/2017 |
| WO | 2017123864 | A1 | 7/2017 |
| WO | 2017147124 | A1 | 8/2017 |

OTHER PUBLICATIONS

He, 2010, Optimal algorithms for haplotype assembly from whole-genome sequence data, Bioinformatics 26:i183-i190.

Heber, 2002, Splicing graphs and EST assembly problems, Bioinformatics 18 Suppl:181-188.

Hein, 1989, A new method that simultaneously aligns and reconstructs ancestral sequences for any number of homologous sequences when the phylogeny is given, Mol Biol Evol 6(6):649-668.

Hein, 1989, A tree reconstruction method that is economical in the number of pairwise comparisons used, Mol Biol Evol 6(6):649-668.

Homer, 2010, Improved variant discovery through local re-alignment of short-read next generation sequencing data using SRMA, Genome Biol 11(10):R99.

Horspool, 1980, Practical Fast Searching in Strings, Software—Practice & Experience 10:501-506.

Huang, Chapter 3: Bio-Sequence Comparison and Alignment, ser. Curr Top Comp Mol Biol. Cambridge, Mass.: The MIT Press, 2002.

Hutchinson, 2014, Allele-specific methylation occurs at genetic variants associated with complex diseases, PLoS One 9(6):e98464.

International Search Report and Written Opinion mailed Aug. 31, 2017, for International Application No. PCT/ US2017/018830 with International Filing Date Feb. 22, 2017, (11 pages).

International Search Report and Written Opinion mailed Mar. 31, 2015 for International Application No. PCT/ US2015/010604 filed Jan. 8, 2015 (13 pages).

International Search Report and Written Opinion mailed Apr. 19, 2017 for International Patent Application No. PCT/US2017/012015, (14 Pages).

International Search Report and Written Opinion mailed Feb. 17, 2015, for International Patent Application No. PCT/US2014/061156, filed Oct. 17, 2014 (19 pages).

International Search Report and Written Opinion mailed Jan. 10, 2017, for International Patent Application No. PCT/US16/57324 with International Filing Date Oct. 17, 2016, (7 pages).

International Search Report and Written Opinion mailed Mar. 19, 2015, for International Application No. PCT/US2014/061162 with International Filing Date Oct. 17, 2014, (12 pages).

International Search Report and Written Opinion mailed May 11, 2015, for International Patent Application No. PCT/US2015/015375 with International Filing Date Feb. 11, 2015, (12 pages).

International Search Report and Written Opinion mailed May 5, 2016, for International Patent Application No. PCT/US2016/020899, wiht International Filing Date Mar. 4, 2016, (12 pages).

(56) References Cited

OTHER PUBLICATIONS

International Search Report and Written Opinion mailed on Apr. 7, 2017, for International Patent Application No. PCT/US17/13329, filed Jan. 13, 2017, (9 pages).
International Search Report and Written Opinion mailed on Dec. 11, 2014, for International Patent Application No. PCT/US14/52065, filed Aug. 21, 2014, (18 pages).
International Search Report and Written Opinion mailed on Dec. 30, 2014, for International Patent Application No. PCT/US14/58328, filed Sep. 30, 2014, (22 pages).
International Search Report and Written Opinion mailed on Feb. 4, 2015, for International Patent Application No. PCT/US2014/061198, filed Oct. 17, 2014, (8 pages).
International Search Report and Written Opinion mailed on Feb. 10, 2015, for International Patent Application No. PCT/US2014/060690, filed Oct. 15, 2014, PCT/US2014/060690 (11 pages).
International Search Report and Written Opinion mailed on Feb. 4, 2015, for Patent Application No. PCT/US2014/061158, filed Oct. 17, 2014, (11 pages).
International Search Report and Written Opinion mailed on Jan. 27, 2015, for International Patent Application No. PCT/US2014/060680, filed Oct. 215, 2014, (11 pages).
International Search Report and Written Opinion mailed Sep. 2, 2016, for International Patent Application No. PCT/US2016/033201 with International Filing Date May 19, 2016, (14 pages).
International Search Report and Written Opinion mailed Sep. 7, 2016, for International Application No. PCT/US2016/036873 with International filing date Jun. 10, 2016, (8 pages).
Kano, 2010, Text mining meets workflow: linking U-Compare with Taverna, Bioinformatics 26(19):2486-7.
Kehr, 2014, Genome alignment with graph data structures: a comparison, BMC Bioinformatics 15:99.
Kent, 2002, BLAT-The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Koolen, 2008, Clinical and Molecular Delineation of the 17q21.31 Microdeletion Syndrome, J Med Gen 45(11):710-720.
Kumar, 2010, Comparing de novo assemblers for 454 transcriptome data, BMC Genomics 11:571.
Kurtz, 2004, Versatile and open software for comparing large genomes, Genome Biol 5:R12.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, Accurate read mapping using a graph-based human pan-genome, ASHG 2014 Abstracts.
Legault, 2010, Learning Probalistic Splice Graphs from RNA-Seq data, pages.cs.wisc.edu/~legault/cs760_writeup.pdf; retrieved from the internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2009, Fast and accurate short read alignment with Burrows-Wheeler Transform. Bioinformatics 25:1754-60.
Li, 2010, A survey of sequence alignment algorithms for next-generation sequencing, Briefings in Bionformatics 11(5):473-483.
Lipman, 1985, Rapid and sensitive protein similarity searches, Science 227(4693):1435-41.
Lucking, 2011, PICS-Ord: unlimited coding of ambiguous regions by pairwise identity and cost scores ordination, BMC Bioinf 12:10.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioninformatics 29 (10):1250-1259.
Barbieri, 2013, Exome sequencing identifies recurrent Spop, FOXA1 and MED12 mutations in prostate cancer, Nature Genetics 44:6 685-689.
Beerenwinkel, 2007, Conjunctive Bayesian Networks, Bernoulli 13(4), 893-909.
Berlin, 2014, Assembling large genomes with single-molecule sequencing and locality sensitive hashing, bioRxiv preprint (35 pages); retrieved from the internet on Jan. 29, 2015.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Browning et al, Haplotype phasing: existing methods and new developments, 2011, vol. 12, Nature Reviews Genetics.
Caboche et al., Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pages iii31-iii38, vol. 21, Oxford University Press.
Chang, 2005, The application of alternative splicing graphs in quantitative analysis of alternative splicing form from EST database, Int J Comp Appl Tech 22(1):14.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Compeau, 2011, How to apply de Bruijn graphs to genome assembly, Nat Biotech 29(11):987-991.
Craig, 1990, Ordering of cosmid clones covering the Herpes simplex virus type I (HSV-I) genome: a test case for fingerprinting by hybridisation, Nucleic Acids Research 18:9 pp. 2653-2660.

(56) References Cited

OTHER PUBLICATIONS

Denoeud, 2004, Identification of polymorphic tandem repeats by direct comparison of genome sequence from different bacterial strains: a web-based resource, BMC Bioinformatics 5:4 pp. 1-12.
DePristo, 2011, A framework for variation discovery and genotyping using next-generation DNA sequencing data, Nat Gen 43:491-498.
Duan et al., Optimizing de novo common wheat transcriptome assembly using short-read RNA-Seq data. (2012) pp. 1-12, vol. 13, BMC Genomics.
Dudley, 2009, A quick guide for developing effective bioinformatics programming skills, PLOS Comput Biol 5(12):e1000589.
Durbin, 2014, Efficient haplotype matching and storage using the positional Burrows-Wheeler transform (PBWT), Bioinformatics 30(9):1266-1272.
Endelman, 2011, New algorithm improves fine structure of the barley consensus SNP map, BMC Genomics 12(1):407 (and whole document).
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Farrar, 2007, Striped Smith-Waterman speeds database searches six times over other SIMD implementations, Bioinformatics 23(2):156-161.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Grasso, 2004, Combining partial order alignment and progressive multiple sequence alignment increases alignment speed and scalability to very large alignment problems, Bioinformatics 20(10):1546-1556.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harrow, 2012, GENCODE: The reference human genome annotation for The ENCODE Project, Genome Res 22:1760-1774.
Lupski, 2005, Genomic disorders: Molecular mechanisms for rearrangements and conveyed phenotypes, PLoS Genetics 1(6):e49.
Ma, 2010, Multiple genome alignment based on longest path in directed acyclic graphs, Int J Bioinformatics 6(4):366-683.
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016.
Marth et al., 1999—A general approach to single-nucleotide polymorphism discovery, pp. 452-456, vol. 23, Nature Genetics.
Mazrouee, 2014, FastHap: fast and accurate single individual haplotype reconstructions using fuzzy conflict graphs, Bioinformatics 30:i371-i378.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Mount, 2001, Multiple Sequence Alignment, Bioinformatics, 2001, Cold Spring Harbor Laboratory Press, Cold Spring Harbor, New York, pp. 139-204.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Nagarajan, 2013, Sequence assembly demystified, Nat Rev 14:157-167.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Newman, 2013, Community detection and graph portioning, Europhys Lett 103(2):28003, arXiv:1305.4974v1.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Oshlack, 2010, From RNA-seq reads to differential expression results. Genome Bio 11:220.
Parks, 2015, Detecting non-allelic homologous recombination from high-throughput sequencing data, Genome Biol 16:17.
Peixoto, 2014, Efficient Monte Carlo and greedy heuristic for the inference of stochastic block models, Phys. Rev. E 89, 012804.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with intersequence SIMD parallelisation, Bioinformatics 12:221.
Ronquist, 2012, MrBayes 3.2: efficient Bayesian phylogenetic inference and model choice across a large model space, Syst Biol 61(3):539-42.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.

(56) References Cited

OTHER PUBLICATIONS

Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 2012, Multiple insert size paired-end sequencing for deconvolution of complex transcriptions, RNA Bio 9(5)596-609.
Sosa, 2012, Next-Generation Sequencing of Human Mitochondrial Reference Genomes Uncovers High Heteroplasmy Frequency, PLoS One 8(10):e1002737.
Sturgeon, RCDA: a highly sensitive and specific alternatively spliced transcript assembly tool featuring upstream consecutive exon structures, Genomics, Dec. 2012, 100(6): 357-362.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, Siam J Comput 22(2):243-260.
Thomas, 2014, Community-wide effort aims to better represent variation in human reference genome, Genome Web (11 pages).
Trapnell, 2009, TopHat: discovering splice junctions with RNA-Seq, Bioinformatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Wang, 2009, RNA-Seq: a revolutionary tool for transcriptomics, Nat Rev Genet 10(1):57-63.
Written Opinion issued in Sg 11201601124Y.
Written Opinion issued in Sg 11201602903X.
Written Opinion issued in Sg 11201603039P.
Written Opinion issued in Sg 11201603044S.
Written Opinion issued in Sg 11201605506Q.
Wu, 2010, Fast and SNP-tolerant detection of complex variants and splicing in short reads, Bioinformatics, 26 (7):873-881.
Xing, 2006, An expectation-maximization algorithm for probabilistic reconstructions of full-length isoforms from splice graphs, Nucleic Acids Research, 34:3150-3160.
Yang, 2013, Leveraging reads that span multiple single nucleotide polymorphisms for haplotype inference from sequencing data, Bioinformatics 29(18):2245-2252.
Yanovsky, 2008, Read mapping algorithms for single molecule sequencing data, Proc 8th Int Workshop Alg Bioinformatics 5251:38-49.
Yu, 2010, The construction of a tetraploid cotton genome wide comprehensive reference map, Genomics 95:230-240.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.

* cited by examiner

SEQUENCE LISTING

<160> NUMBER OF SEQ ID NOS: 4

<210> SEQ ID NO 1
<211> LENGTH: 9
<212> TYPE: DNA
<213> ORGANISM: Homo sapiens

<400> SEQUENCE: 1

```
gaggattct                                                             9

<210> SEQ ID NO 2
<211> LENGTH: 9
<212> TYPE: DNA
<213> ORGANISM: Homo sapiens

<400> SEQUENCE: 2 gaggaccct                                                             9

<210> SEQ ID NO 3
<211> LENGTH: 9
<212> TYPE: DNA
<213> ORGANISM: Homo sapiens

<400> SEQUENCE: 3 gaacattct                                                             9

<210> SEQ ID NO 4
<211> LENGTH: 9
<212> TYPE: DNA
<213> ORGANISM: Homo sapiens

<400> SEQUENCE: 4 gaacaccct                                                             9
```

SYSTEM AND METHOD FOR SEQUENCE IDENTIFICATION IN REASSEMBLY VARIANT CALLING

RELATED APPLICATIONS

This application claims priority to U.S. Provisional Patent Application Ser. No. 62/630,347 filed on Feb. 14, 2018, the contents of which are hereby incorporated by reference in its entirety.

SEQUENCE LISTING

This application contains a sequence listing which has been submitted in ASCII format via EFS-Web and is hereby incorporated by reference in its entirety. The ASCII-formatted sequence listing, created on May 13, 2019, is named SBG-083-01USSequences_ST25.txt, and is 1,024 bytes in size.

FIELD

Aspects of the technology described herein relate to nucleotide sequence alignment and assembly in bioinformatics, genomics, and related disciplines.

BACKGROUND

Variant calling refers to a process of identifying differences, or variations, between a sample and a reference. The sample can be a genomic sample, such as genomic DNA from an individual, and the reference can be a suitable reference sequence for comparison to the sample, such as one of the available human genome reference sequences. Typically, variant calling is performed by aligning a set of sequence reads to the reference using sequence alignment software, such as the Burrows Wheeler Aligner (BWA), Bowtie, or a graph-based aligner such as the Seven Bridges Graph Genome Suite. Any differences between the aligned sequence reads and the reference may further be analyzed for evidence of variation.

Typically, an aligner annotates each sequence read with an alignment indicator, such as a Concise Idiosyncratic Gapped Alignment Report (CIGAR) string. The CIGAR string indicates any differences between the read and the reference, such as mismatches, insertions, deletions, soft-clips, or other differences. These events are taken as evidence of the presence of variants. Most variant callers (e.g., FreeBayes) aggregate these events and call variants based on certain thresholds. Variants may be further analyzed for, e.g., association with disease, genetic traits, and the like.

However, in some genomic samples, regions of the sample sequence may significantly differ from the reference sequence. For example, the genomic sample sequence may include large structural variations, or a number of small variations sufficiently close together to confuse alignment and traditional variant calling. Similarly, many populations (such as individuals of African descent) may have genomes that are not well represented by the reference. In such cases, regions of the sample sequence lacking sufficient homology to the reference will lead to unmapped or incorrectly placed sequence reads, and ultimately will fail to identify the correct sequence for that region.

However, often sequence reads which lack homology may still partially align to the correct region, providing useful information from which one can infer the correct sequence. One approach for dealing with such troublesome regions is to assemble the sequence for a given region de novo directly from the sequence reads. De novo assembly is complicated and computationally expensive, particularly so for relatively large genomes such as the human genome. Typically, variant calling is performed using "local" assembly, which involves assembling sequence reads from only a relatively small region exhibiting suspected variation. The correct sequence for that region in the genomic sample is reassembled from the sequence reads and then compared to the reference to identify the true variation. Such reassembly-based variant callers may be used to identify high quality variations in reference alignments in which the degree of homology to the reference is low or variable. However, reassembly adds considerable complexity and requires a significant amount of computational resources to scale to the analysis of whole genomes, such as the human genome. Accordingly, there is a need for improvements in reassembly-based variant calling.

SUMMARY

Variant calling processes that incorporate reassembly provide for the accurate identification of the "true" sequence for a genomic region of interest within a genomic sample. However, the inventor has recognized and appreciated that conventional techniques for reassembly may be improved upon because they are computationally expensive due to the large number of candidate sequences that must individually be considered. Thus, the inventor has recognized that the problem of evaluating candidate sequences for reassembly is solved by a method that scores variant sites in an assembly graph in the context of a current path—i.e., the current haplotype or candidate sequence that is being considered that includes that variant. This leads to an improvement in accuracy that allows for the number of candidate sequences through the graph to be evaluated to be significantly reduced, resulting in an improvement in computational efficiency.

In one embodiment, a system for identifying candidate sequences for genotyping a genomic sample, the system comprises at least one computer hardware processor, and at least one non-transitory computer-readable storage medium storing processor-executable instructions. When executed by the at least one computer hardware processor, the at least one computer hardware processor obtains a plurality of sequence reads mapping to a genomic region of interest and assembles a directed acyclic graph (DAG). The DAG comprises a plurality of branch sites representing variation present in the set of sequence reads, each branch site comprising two or more branches. A path through the graph comprises a set of successive branches over two or more branch sites and represents a possible candidate sequence of the genomic sample. One or more paths through the DAG are ranked by calculating scores for one or more branch sites, wherein the calculated score comprises a number of sequence reads that span multiple branch sites in a given path. At least one path is selected as a candidate sequence based at least in part on its rank.

In some embodiments, calculating a score for a branch site comprises calculating a ratio of: the number of sequence reads that align to both a first branch of a first branch site and a first branch of a second branch site, over the number of sequence reads that align to both the first branch of the first branch site and the first branch of the second branch site, and the number of sequence reads that align to both the first branch of the first branch site and a second branch of the second branch site. In some embodiments, the one or more paths are ranked based on the product of scores for each branch in that path. In some embodiments, the DAG is a de Bruijn-like graph, and wherein creating the DAG further comprises representing k-mers present in the set of sequence reads as nodes and connections between those k-mers in the set of sequence reads as edges. In these embodiments, the assembling further comprises excluding k-mers having a low probability of being error-free. In these embodiments, the excluded k-mers may have a probability of being error-free less than $0.995^k$.

In some embodiments, selecting at least one path as a candidate sequence further comprises selecting a plurality of paths as a plurality of candidate sequences based at least in part on their rank. In these embodiments, 25 or fewer candidate sequences may be selected. In some embodiments, a candidate sequence is aligned to a reference sequence to identify a variation in the genomic sample. In these embodiments, variants from the candidate sequence can be evaluated using a pair Hidden Markov Model (pair HMM).

In some embodiments, the candidate sequence represents a possible haplotype of the genomic sample. In some embodiments, the plurality of nucleotide sequence reads are obtained from a reference alignment of the genomic sample against a reference genome, and the genomic region of interest comprises a subsection of the reference alignment indicative of variation of the genomic sample from the reference genome. In these embodiments, the identified subsections of the reference alignment may be those in which a plurality of sequence reads indicate variation from the reference sequence. In these embodiments, the variation from the reference sequence may be identified using a CIGAR string. In these embodiments, the identified subsection may be about 300 base pairs long. In some embodiments, ranking one or more paths through the DAG further comprises traversing the DAG and identifying one or more partial paths, each partial path comprising one or more nodes; selecting partial paths with highest read support for continued traversal to identify one or more completed paths; storing a threshold number of the one or more completed paths; and selecting at least one completed path as a candidate sequence once the identified one or more partial paths have less read support than the threshold number of the one or more completed paths.

In another embodiment, a method of identifying candidate sequences for genotyping a genomic sample comprises assembling, from a plurality of sequence reads mapping to a genomic region of interest, a directed acyclic graph (DAG). The DAG comprises a plurality of branch sites representing variation present in the set of sequence reads, each branch site comprising two or more branches. A path through the graph comprises a set of successive branches over two or more branch sites and represents a possible candidate sequence of a genomic sample. One or more completed paths through the DAG are ranked by calculating scores for a plurality of partial paths, wherein the partial paths are followed to become complete paths by considering whether the plurality of partial paths have less read support than the one or more completed paths. At least one completed path is selected as a candidate sequence based at least in part on its rank.

In some embodiments, ranking one or more completed paths through the DAG further comprises maintaining a queue of partial paths through the DAG, each partial path comprising one or more connected nodes, selecting a highest scoring partial path from the queue of partial paths, and traversing the DAG from the last node in the partial path. The traversal can include following outgoing edges from the last node and adding encountered nodes to the partial path. A branching point may be encountered that comprises a node having two or more child nodes. Two or more partial paths are created based on the partial path and the encountered branching point, and a score is calculated for each of the two or more partial paths. The created two or more partial paths are then added to the queue of partial paths.

In some embodiments, ranking one or more completed paths through the DAG further comprises selecting a highest scoring partial path from the queue of partial paths, and traversing the DAG from the last node in the partial path, the traversal comprising following outgoing edges from the last node and adding encountered nodes to the partial path. A node may be encountered having no outgoing edges, and a score is calculated for the partial path. The partial path is then added to a second queue of complete paths. In these embodiments, selecting at least one path as a candidate sequence based at least in part on its rank comprises selecting one or more paths from the second queue of complete paths as one or more candidate sequences.

BRIEF DESCRIPTION OF THE DRAWINGS

Various aspects and embodiments will be described with reference to the following figures.

The figures are not necessarily drawn to scale.

DETAILED DESCRIPTION

The present disclosure describes various new techniques that may be used in the context of variant calling and identification processes that re-assemble portions of a reference sequence from a corresponding set of aligned sequence reads. Variant calling processes that incorporate reassembly typically include identifying genomic regions of interest in a reference alignment, constructing an assembly graph from the sequence reads in that region, and then identifying paths through the assembly graph as candidate sequences. However, the inventor has recognized and appreciated that conventional methods of reassembly are inefficient and can be improved upon. For example, typically every path through the graph must be evaluated in order to identify the best set of candidate sequences. This is compounded by the nature of the assembly graph, in which any variation in the sequence read dataset leads to an exponential number of paths.

Accordingly, the inventor has developed a new class of techniques for performing reassembly which improves both the speed and accuracy of variant calling. The new class of techniques can involve trimming nodes from an assembly graph based on the probability that a k-mer is error-free, thus significantly reducing the number of nodes (and paths) from consideration. Further, the new class of techniques can involve scoring paths based on whether sequence reads span branching points within the graph, providing evidence that certain variations are linked with one another. This leads to an increase in accuracy in path evaluation that allows for fewer than the total number of paths through the graph to be evaluated, identifying the most likely set of candidate sequences for the genomic regions of interest, while using less time and computational resources.

Some embodiments described herein address all of the above-described issues that the inventor has recognized with conventional techniques for variant calling and reassembly. However, not every embodiment described herein addresses every one of these issues, and some embodiments may not address any of them. As such, it should be appreciated that embodiments of the technology described herein are not limited to addressing all or any of the above-discussed issues of conventional techniques for variant calling and reassembly. It should be appreciated that the various aspects and embodiments described herein may be used individually, all together, or in any combination of two or more, as the technology described herein is not limited in this respect.

I. Exemplary Variant Calling Service

Figure 1:
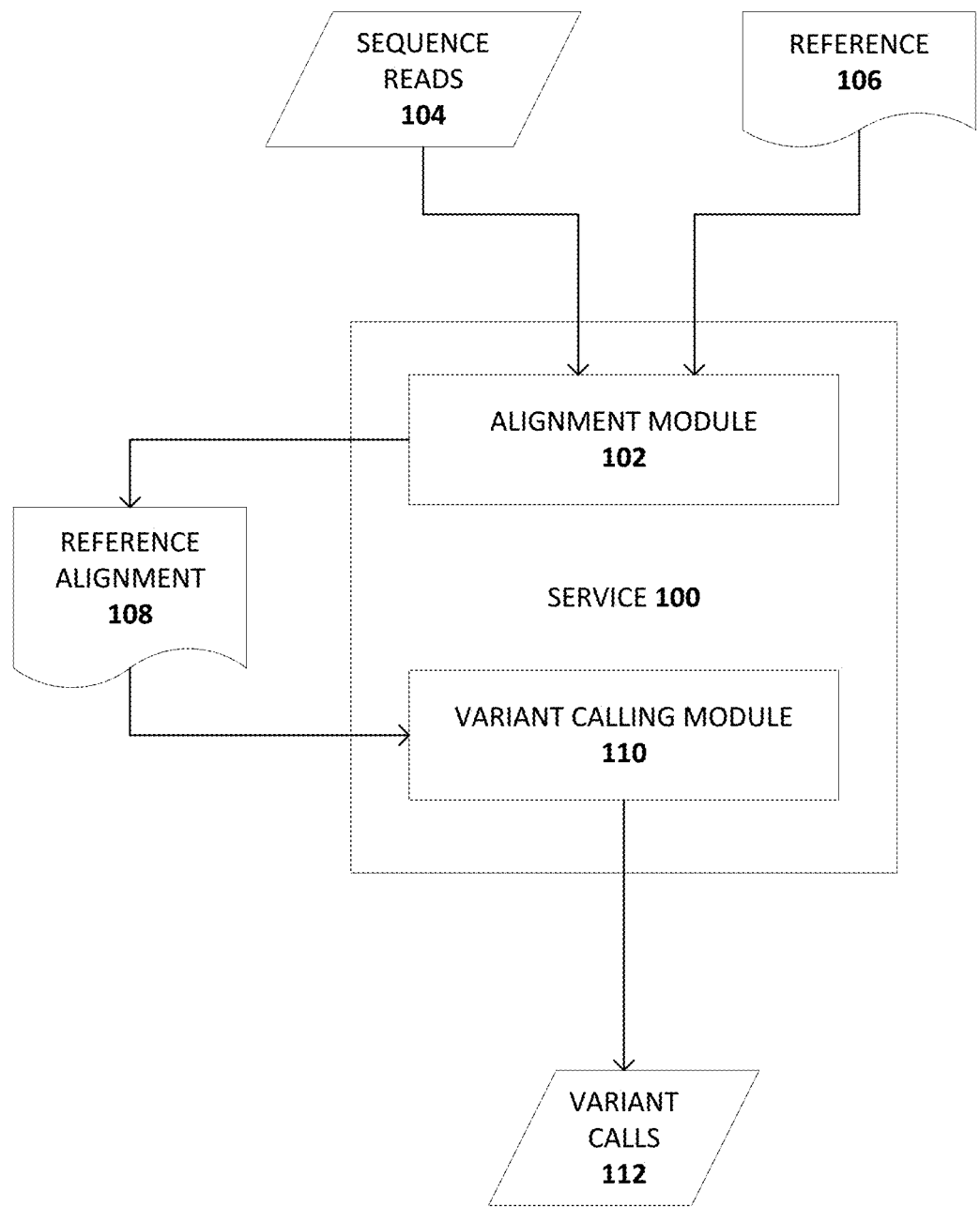
FIG. 1 is a block diagram illustrating an embodiment of a representative variant calling service according to the disclosure.

The general approach taken by embodiments of the present invention is illustrated in FIG. 1, which illustrates, in block-diagram form, an exemplary variant calling service 100 with features enabling fast and accurate variant calling. The service 100 may include an alignment module 102, which can align a set of sequence reads 104 from a sample to a reference 106. The result of an alignment is a reference alignment 108, which describes the positioning of the sequence reads 104 with respect to the reference 106. The reference alignment 108 may further be processed by a variant calling module 110, which scans the reference alignment to identify positions in which the sequence reads differ from the reference 108, such as single nucleotide polymorphisms (SNPs), insertions and deletions (INDELs), and structural variations (SVs). Such variants 112 may then be analyzed for, e.g., markers for disease, association with certain traits, and the like.

Each sequence read 104 may comprise a sequence of contiguous nucleotide bases, which may symbolically be represented by the letters A, C, G, and T. The contiguous nucleotide bases represent a sequence that is "read" from a corresponding genomic sample, such as a DNA sample, RNA sample, ChIP-Seq sample, and the like. Typically, the sequence reads 104 will be obtained with the aid of a sequencer instrument, such as, for example, a Next Generation Sequencer (NGS) sequencer. Sequencing technologies and instruments are known in the art and include, for example, MiSeq® (Illumina, San Diego, CA), Ion Torrent® (Life Technologies, Carlsbad, CA), 454® (454 Life Sciences, Roche, Branford, CT), SOLiD® (Applied Biosystems, Thermo Fisher Scientific, Foster City, CA), tSMS™ (Helicos BioSciences, Cambridge, MA), SMRT® (Pacific Biosciences, Menlo Park, CA), and chemFET techniques. Sequence reads 104 are often stored in an electronic format, such as in a FASTA or FASTQ file.

In general, a nucleotide sequence read 104 that is being analyzed according to the disclosure will have a length of about 50 to about 500 nucleotides. For example, a nucleotide sequence read can have a length of about 50, about 100, about 150, about 200, about 250, about 300, about 350, about 400, about 450, or about 500 nucleotides. In some embodiments, sequence reads 112 include at least 50 base pairs (e.g., 50 base pairs, 100 base pairs, 200 base pairs, 500 base pairs). In further embodiments, sequence reads 104 may be longer (e.g., 100 base pairs or more, 500 base pairs or more, 1,000 base pairs or more, 5,000 base pairs or more, and 10,000 base pairs or more). For example, certain "long read" next-generation sequencing technologies, such as PacBio® Single Molecule, Real-Time (SMRT) Sequencing, can generate sequence reads that range from 10,000 to 60,000 base pairs. Certain sequencing technologies can also generated "paired-end" reads, in which both the 5' and 3' ends of a DNA molecule are sequenced, often leading to an inferred distance between the ends that may be used to help align sequence reads in repetitive regions.

The goal of sequence alignment is to identify the most likely position for each sequence read against a reference sequence, such as the reference 106. The reference 106 can be any nucleotide or protein sequence, and typically will be much longer (e.g., 1 kb-1 tb) than the average length of the sequence reads 104. For example, the reference 106 can be the human GRCh38/hg38, mouse GRCm38/mm 10, and Zebrafish GRCz11/danRer11 reference genomes, available from the UCSC Genome Browser at hgdownload.cse.ucsc.edu/downloads.html. In some embodiments, the reference 106 can be a graph-based reference, in which a reference sequence and known variation of the reference sequence are represented as diverging paths through a graph. Examples of graph-based references can be found in U.S. Pat. No. 9,898,575, filed on Sep. 3, 2013, the contents of which are hereby incorporated by reference.

The alignment module 102 identifies the best mapped position for each sequence read 104 against the reference 106. There are many different algorithms for sequence alignment. For example, the Smith-Waterman algorithm is a dynamic programming algorithm that identifies an optimal alignment between two sequences by scoring two sequences in a matrix and identifying an optimal back-trace. However, such algorithms are typically too slow to be useful for aligning sequences to whole genome references, which can be billions of bases in length. Other algorithms account for this issue by identifying possible locations for a read using a hash table, Burrows-Wheeler transform, and other methods. The read is subsequently aligned to those possible locations using a "local" algorithm (such as Smith-Waterman). Sequence reads may also be aligned to graph references using a multi-dimensional algorithm that considers and scores multiple paths, such as those described in U.S. Patent Publication No. 2018/0137387, filed Nov. 16, 2016, the contents of which are hereby incorporated by reference.

The result of sequence alignment is typically a reference alignment 108, which includes information describing the positioning of each of the plurality of sequence reads 104 against the reference 106. FIG. 2A illustrates the reference alignment 108 of FIG. 1 in more detail. As shown, the reference alignment 108 includes a portion of the reference 106 and several of the plurality of sequence reads 104. Each of the sequence reads 104 is positioned at its most likely source of origin from the reference 106, as determined by (e.g.) an alignment module according to the disclosure. At each position in the reference, the number of corresponding bases from aligned sequence reads can be counted to generate a coverage chart 202, indicating how often that particular base was sequenced. Often, many mapped bases differ from the reference sequence. These bases are evidence of variation within the sequence reads, which may be a result of real variation in a genomic sample, or error related to either the sequencing or alignment process. If a sufficient number of bases differ from the reference at a position, a variant may be called. For example, the reference alignment 108 suggests the presence of four heterozygous SNPs 204.

Figure 3:
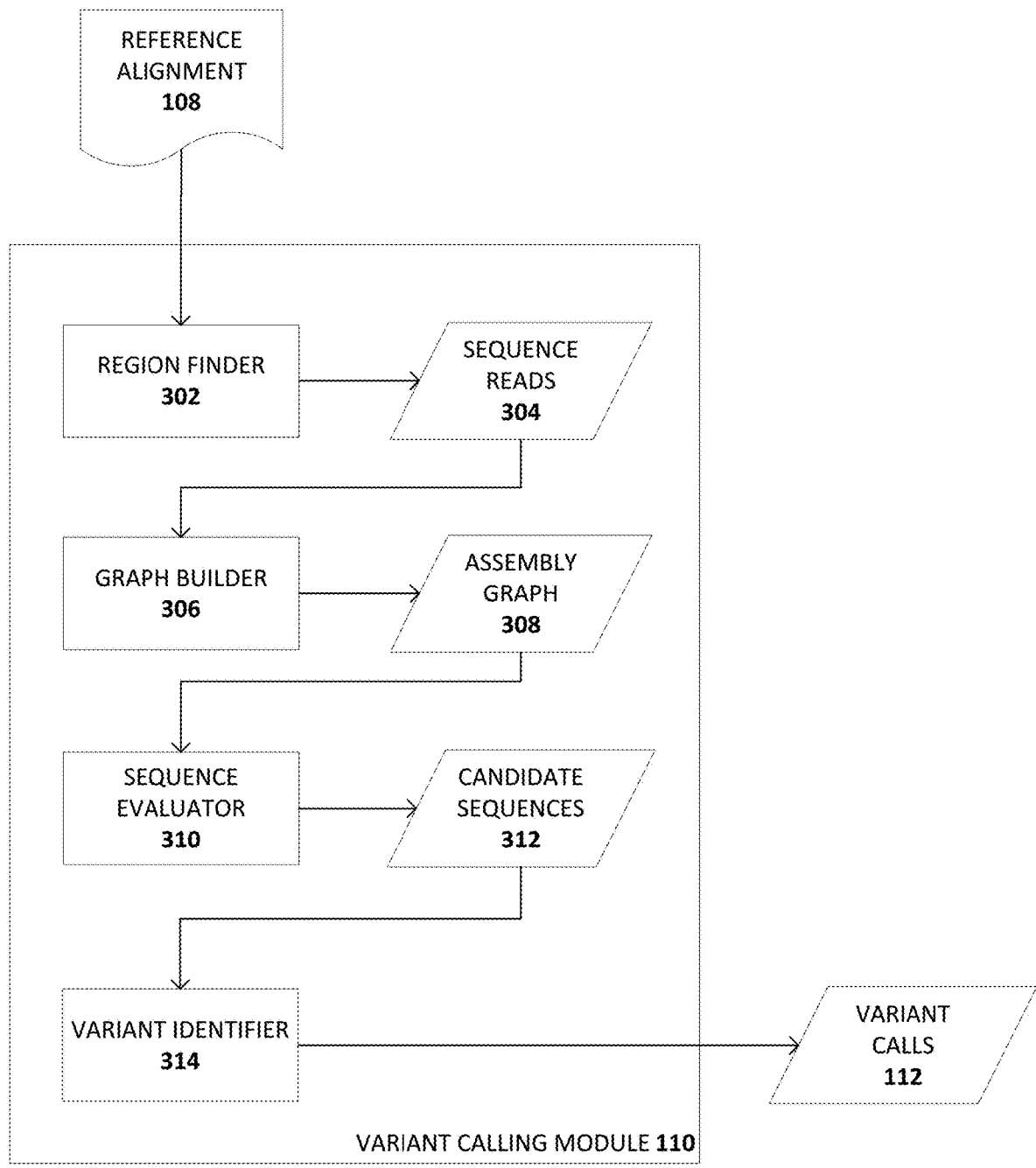
FIG. 3 is a block diagram illustrating an embodiment of a variant calling module according to the disclosure.

Such SNPs and other variations present in the sequence data may be identified by the variant calling module 110. In one embodiment, the variant calling module 110 reassembles portions of the reference sequence 106 based on the alignment of the sequence reads 104 to yield high quality variant calls 112. FIG. 3 illustrates the variant calling module 112 of FIG. 1 in further detail. As shown, the variant calling module 110 further comprises a region finding module 302, a graph building module 306, and a candidate sequence evaluating module 310. From the reference alignment 108, the region finding module 302 identifies genomic regions of interest by scanning the reference alignment for regions indicating a lack of homology to the reference. For each identified region, a set of sequence reads 304 corresponding to that region are provided to the graph building module 306 and assembled into an assembly graph 308. High scoring paths, corresponding to candidate sequences for the genomic region of interest, are identified by the candidate sequence evaluating module 310 to yield a high quality set of candidate sequences 312. Each candidate sequence 312 corresponds to a possible "true" sequence for the genomic region of interest. A variant identification module 314 may then align candidate sequences 312 against the reference sequence for the genomic region of interest using an optimal alignment algorithm (e.g., Smith-Waterman) and any differences may be parsed into a set of variant calls 112.

Figure 4:
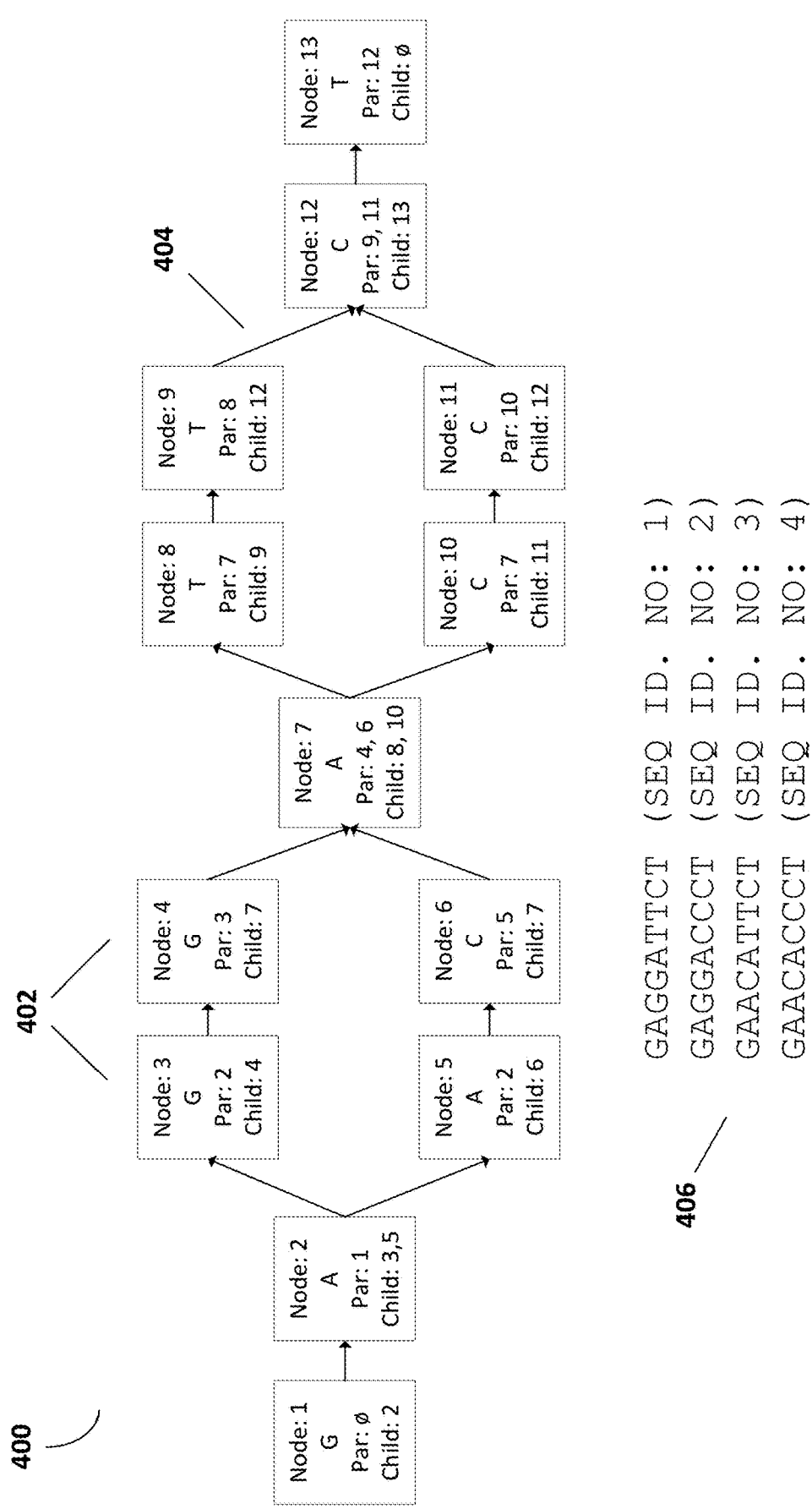
FIG. 4 is an illustration of an embodiment of an assembly graph according to the disclosure.

FIG. 4 illustrates an example of an assembly graph 400 according to the disclosure. As shown in FIG. 4, the assembly graph 400 comprises a plurality of nodes 402 connected by edges 404. Each of the nodes 402 is associated with a nucleotide sequence, and may include information regarding any parent or child nodes of that node. As shown, the nucleotide sequence for each node is a single symbol, though nodes having multiple symbols are possible. Candidate sequences can be generated by traversing paths through the graph and concatenating the nucleotide sequences from nodes in that path into a concatenated sequence. (Note that in the case of DeBruijn-like graphs, the nodes typically represent k-mers, and thus overlaps between k-mers may be excluded to yield the candidate sequence.) In this example, the assembly graph 400 has four different paths, corresponding to four different candidate sequences 406. In a diploid sample, one or two of these sequences may represent the true haplotypes present in the sample.

In practice, the assembly graph 400 may be represented and stored in a computer memory. For example, a node can be a portion of the memory, which can include entries within a database, files, or portions of one or more files within a file system. More specifically, a node can be one or more memory locations at which properties or characteristics of that node (e.g., an associated nucleotide sequence) and references or relationships between that node and other nodes (e.g., connections to parent or child nodes) are stored. As a specific example, a node can be a portion of a memory at which a list of edges of that node (or edges adjacent to or incident upon that node) are stored.

II. Exemplary Variant Calling Methods

Figure 5:
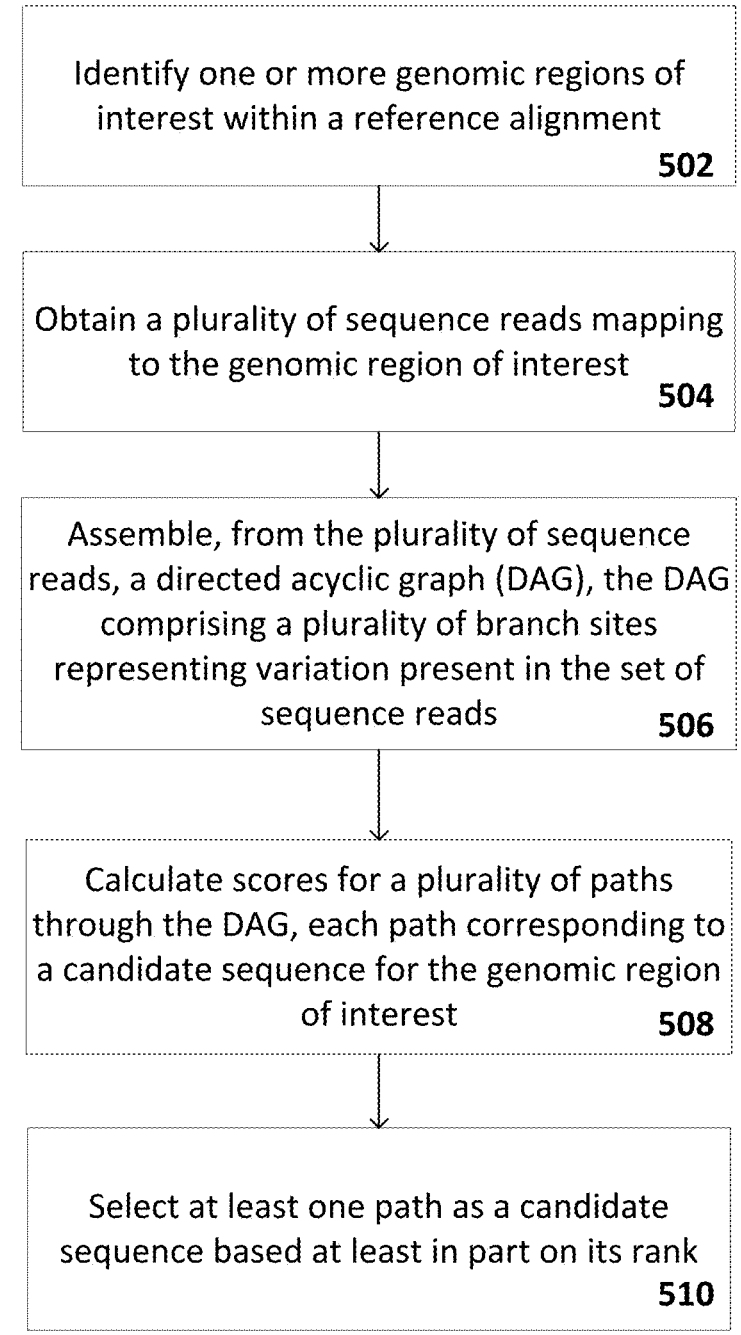
FIG. 5 is a flow diagram depicting a method of reassembling a reference sequence from a reference alignment.

FIG. 5 depicts a method 500 of calling variants from a reference alignment according to an embodiment of the disclosure. The method 500 can begin by identifying one or more genomic regions of interest within a reference alignment (step 502). Each region typically comprises a set of sequence reads (step 504), which may be assembled against one another to form an assembly graph (step 506). Paths through the graph (corresponding to candidate sequences for the genomic region of interest) are scored and ranked (step 508). Based on the ranking, at least one candidate sequence is selected as the reassembled sequence for that genomic region of interest (step 510). These steps are discussed in further detail below.

Identifying Regions for Reassembly in the Reference Alignment

Identifying regions within a reference alignment for local reassembly (step 502) can include scanning a reference alignment for regions showing evidence of variation. This may involve identifying regions where the evidence of variation suggests that the real variation has not been captured by the reference alignment, such as in the case of variations longer than a few nucleotides. However, in some embodiments, all variations may be selected for reassembly. One exemplary algorithm for identifying regions is performed by the Genome Analysis Toolkit (GATK, Broad Institute), which searches a reference assembly for "active regions". Active regions are regions within a reference alignment in which the aligned sequence reads show substantial evidence of variation relative to the reference. Regions in which a smoothed average of variation exceeds a threshold level are selected for reassembly.

In one embodiment, a first set of variations from the reference are initially identified from an alignment indicator associated with each sequence read. The alignment indicator can be, for example, a Concise Idiosyncratic Gapped Alignment Report (CIGAR) string (i.e., as described in the Sequence Alignment/Map Format Specification). At each position in the reference alignment, the set of CIGAR strings are collected and a score is calculated based on the number of sequence mismatches and/or INDELS at that position. For each sequence mismatch, a score can be generated based on the phred-scaled base quality (BQ) for that base, or in the case of INDELS an arbitrary score, e.g. 45. The scores are summed and compared to three times the number of aligned reads at that position. If the score exceeds that threshold, the position is identified as a possible variant. This process is similar to traditional linear variant calling techniques (such as FreeBayes, available at github.com/ekg/freebayes), and yields a first set of high quality variants on the reference alignment. This first set of variants can be further processed to infer the presence of substantial variation that may require re-assembly.

Regions of the reference assembly having a large number of possible variants are likely to have a more substantial variation that is not accurately captured by the reference alignment. Such variations may be better identified by re-assembling the reads within that genomic region of interest. For example, in one embodiment, a smoothed average of the number of variants or scores associated with the variants can be used to infer variation wither the average exceeds a threshold value.

In another embodiment, regions can be identified using two pointers on the reference alignment, with one pointer trailing the other by a short distance (e.g., 100-500 bp, preferably 300 bp). Starting from the beginning of the reference (or other specified interval), the two pointers scan along the reference and identify regions with substantial variation. The first pointer can be considered a "window formation pointer", and as it encounters variants from the first set it stores the location of that variant as a "variant window." The second pointer, trailing behind, then encounters variant windows successively and combines those sufficiently close to one another (e.g., less than 15 bp) into larger "assembly windows." The assembly windows are successively merged until either all of the nearby variant windows are included, or until the resulting assembly window size reaches a maximum threshold (e.g., 300 bp). One of the benefits of this two-pointer system is that the entire set of aligned reads (which can be quite large) does not need to be loaded into memory, allowing for the use of less resources. Additionally, merging nearby variants into the same assembly window or region helps to prevent redundant assemblies, as often the same sequence reads will be included to account for those variants.

Once identified, each region or assembly window can be defined by a set of sequencing reads aligned to that window, and the region of the genome (e.g., the start and end position, chromosome, and/or reference sequence) that the window represents. Assembly window sizes vary, but are typically in the range of 300 bp. Once identified, the assembly window is submitted to an assembly algorithm to identify a set of candidate sequences for that region. The second pointer then continues one position past the last variant encountered, identifying further assembly windows in the reference alignment to be re-assembled.

Figure 2:
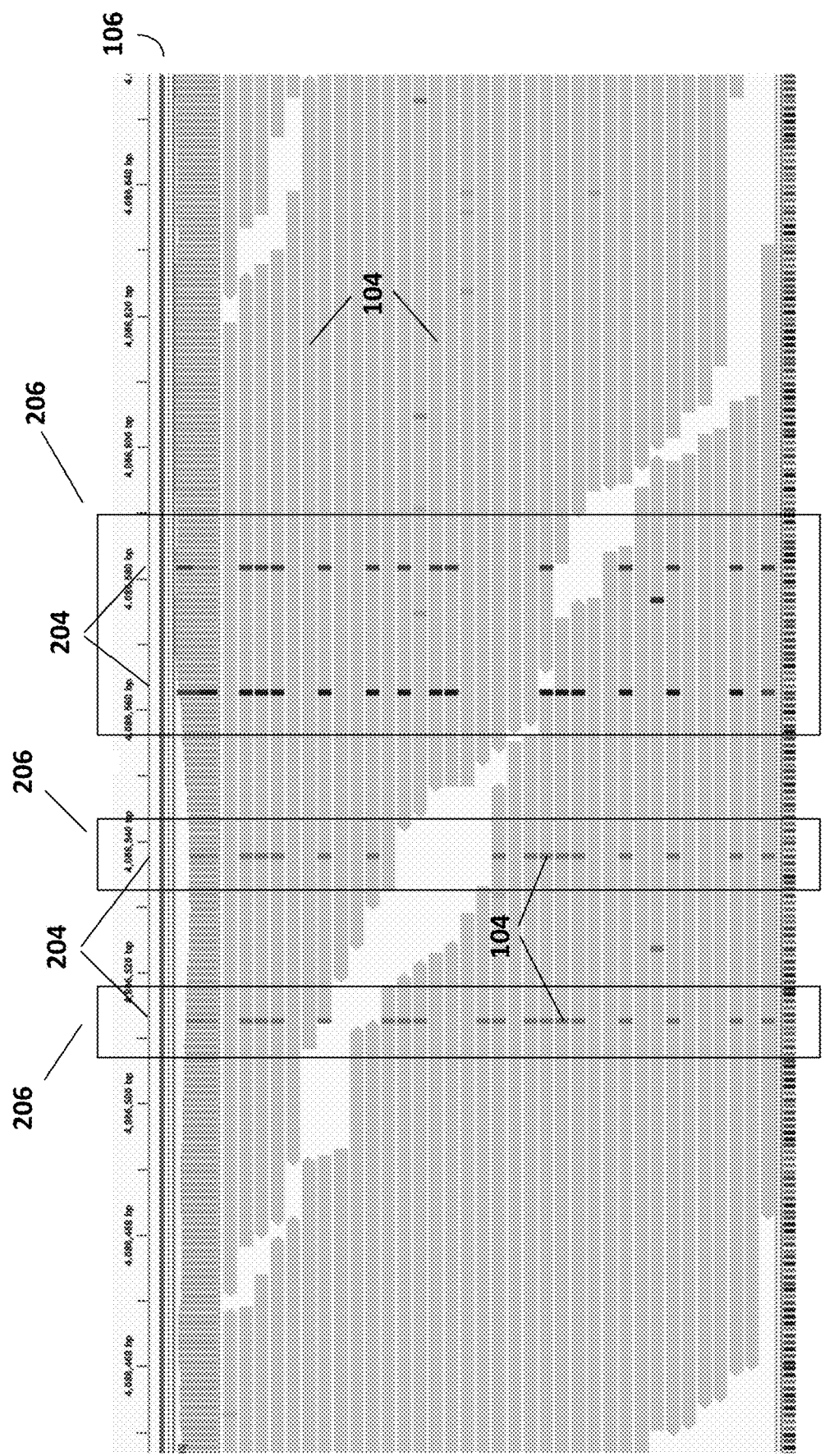
FIG. 2 depicts an illustration of a reference alignment of a plurality of sequence reads against a nucleotide sequence.

As shown in FIG. 2, variant windows 206 may be identified from a plurality of identified variants 204 in a reference alignment 106. Each window 206 corresponds to a region of the reference that can be reassembled by assembling each of the sequence reads 104 mapping to that region. As shown, variant windows may include multiple identified variants, as it is possible that several variants close together indicate a larger variation not accurately captured by the reference alignment. These regions represent a genomic region of interest that may be reassembled into the "true" sequence for the corresponding sample from which the sequence reads were generated.

Constructing an Assembly Graph from Sequence Reads within the Assembly Window

Once a genomic region of interest is identified for local assembly, the sequence reads within that region can be obtained (step 504) and assembled against one another in order to identify the "true" sequence for that region (step 506). The assembly may be de novo (i.e., performed without the reference sequence) or assisted (including the reference sequence). There are many ways to perform sequence assembly, such as the Overlap Layout Consensus (OLC) approach which identifies a consensus sequence from overlaps between sequence reads. Additionally, there are various graph-based approaches which involve building an assembly graph (e.g., an overlap graph, a de Bruijn graph, and the like) from the sequence reads. Paths through the assembly graph represent possible assembled sequences from the assembly window, which can correspond to possible sequences present in the genomic sample. Examples of de novo assembly can be found at least in Florea and Salzberg, "Genome-Guided Transcriptome Assembly in the Age of Next-Generation Sequencing", IEEE/ACM Trans. Comput. Biol. Bioinform. 10(5):1234-1240 (2015), and Duan et al., "Optimizing de novo common wheat transcriptome assembly using short-read RNA-Seq data", BMC Genomics 13:392 (2012).

One type of assembly graph is a de Bruijn-like graph, which is built from k-mers present in the sequence reads. First, all of the sequence reads within the assembly window may be collected and k-mers within the reads are identified. Unique k-mers are represented as nodes. Overlaps between k-mers within the reads are then represented as edges connecting those corresponding nodes. Positions at which the k-mers within the reads diverge are specified as edges connecting to alternate nodes. The edges specify a plurality of paths that may be taken through the graph, where each path describes a possible contiguous sequence for that assembly window. Optionally, one may also include the reference sequence (and its k-mers) in the assembly graph; this can be helpful if there are repetitive regions in the reference or sample, though it also may bias the assembly towards the reference. Preferably, a constructed de Bruijn-like graph has one source node and one sink node, which correspond to the first and last k-mers in the assembly window, respectively.

Once built, the de Bruijn-like graph is traversed to identify paths, which correspond to possible sequences present in the genomic sample. As the human genome is diploid, there may be two different "true" sequences, and therefore two true paths through the graph, in any given region. These sequences correspond to each copy of a chromosome, and may be referred to as "haplotypes" or "haplotype sequences." However, identifying the two true paths is complicated by the nature of the graph because the number of available paths through a graph increases exponentially with the number of possible variations. For example, a graph containing possible variations at three sites will have $2^3$ possible paths.

This problem is compounded by the nature of next-generation sequencing data, which is typically noisy. Most of the variation seen in a typical sequencing data set is due to error, rather than true variation. Including all variation shown in the sequencing data results in a complex graph that requires excessive computing resources to traverse and identify valid candidate sequences. Graphs can be pruned to some extent to help reduce the number of possible paths. For example, after the graph is constructed, nodes having low support (which likely represent error) may be pruned. As a specific example, nodes or regions of the graph may be removed if they are (A) supported by only a single read, or (B) not reachable from both the start and end nodes of the graph.

Similarly, read base qualities may be used to determine whether certain k-mers are added to the graph, such that unreliable read regions are excluded from consideration. For example, one version of GATK explicitly discards any k-mer from consideration that has a base with low quality. However, the inventor has recognized and appreciated that removing k-mers may also reduce sensitivity, particularly in lower coverage datasets. One way to provide a good balance between sensitivity and specificity, while still resulting in a smaller assembly graph, is to consider the quality of the entire k-mer rather than on a per-position basis. If that k-mer is of a certain quality overall, it may be included regardless of whether individual bases have low quality.

Base quality (BQ) is a measure of the quality of the identification made by the underlying next-generation DNA sequencing process. BQ is logarithmically related to the probability of a base-calling error at that position. For example, a BQ of 10 indicates that there is a 10% chance of an error, and a BQ of 30 indicates a 0.1% chance.

$$BQ = -10\log_{10}P(\text{error}), \text{ or}$$

$$P(\text{error}) = 10^{\frac{-BQ}{10}}$$

Similarly, the probability that a base is correct is:

$P(\text{base correct}) = 1 - P(\text{error})$

If $BQ_i$ is the base quality of the ith base within a k-mer, then the probability that the k-mer is error-free is:

$$P(kmer \text{ is error free}) = 1 - \prod_{i=1}^{k} 1 - 10^{\frac{-BQ_i}{10}}$$

This probability can be compared to a threshold value to determine whether to include a k-mer in an assembly graph. Preferably, this value is adjusted to provide a constant error rate per base regardless of the length of the k-mer, as shown:

$P(kmer \text{ is error free}) < 0.995^k$ k-mers that fall below this threshold can be discarded. We find that the above metric is superior and produces better results than simply considering k-mers on a per-position basis. The threshold value (0.995) is empirically derived based on current benchmarks; however a range of values from 0.985-0.998 also works well.

Table I (below) compares results from a prior art method in which k-mers are discarded from an assembly graph if any base has a BQ score of less than 10 ("Experiment 1"), and a method according to the disclosure in which the probability that a k-mer is error-free ($<0.995^k$) is substituted. As shown, there are significant improvements in precision and F-measure, with only a slight decrease in recall for every category.

filtering methods exist to reduce the number of false positives (FPs) from resulting variant calls, these methods are not able to consider variants that were not called at all.

Selecting Paths Through the Assembly Graph as Candidate Haplotypes

Once an assembly graph is created for a genomic region of interest, candidate haplotype sequences can be identified by traversing the graph (e.g., by a depth-first search) to identify a plurality of paths. Every path through the graph from source to sink represents a possible sequence that starts at the beginning of the assembly window and stops at the end (meaning that all potential haplotypes start and stop at the same location on the reference, which aids with variant annotation). These candidate sequences represent estimates of sequences from the underlying genomic sample within the reassembly window.

When there are many variants or errors in the data or the window is very long, many paths can result. This can be greater than the number of paths that can be processed in a reasonable amount of time. Methods of the disclosure allow for a subset (e.g., 20) of the most likely candidate sequences to be identified and processed. As described in more detail below, each path can be scored by computing the ratio of reads overlapping consecutive variants (and supporting both alleles), over the total number of reads overlapping both variants and supporting the first allele (without regard to whether they support the second). Each ratio calculated for a candidate sequence can be multiplied to derive its score.

Evaluating Read Support at Variations

Paths can be evaluated by considering the amount of sequence read support at each variation. By weighting

TABLE I

| | All | | | SNP | | | INDEL | | |
|---|---|---|---|---|---|---|---|---|---|
| Experiment | Precision | Recall | F-measure | Precision | Recall | F-measure | Precision | Recall | F-measure |
| 1 | 99.7862 | 99.9360 | 99.8610 | 99.8092 | 99.9560 | 99.8825 | 99.6348 | 99.8048 | 99.7198 |
| 2 | 99.8223 | 99.9355 | 99.8788 | 99.8467 | 99.9558 | 99.9012 | 99.6613 | 99.8025 | 99.7318 |
| Improvement | 0.0361 | −0.0005 | 0.0178 | 0.0375 | −0.0002 | 0.0187 | 0.0265 | −0.0023 | 0.012 |

The presence of loops, or cycles, in a graph can also hinder the identification of candidate sequences by allowing for indeterminate sized candidate sequences. Loops typically result from the presence of non-unique k-mers that correspond to different regions of the underlying sequence. Using a large k-mer size can eliminate loops, but can also exacerbate the effects of sequencing errors, low quality bases, and limited read lengths. Accordingly, we find that moderately sized k-mers—e.g., from 15-85, increasing in increments of 10—work well for Illumina sequencing data. Additionally, for sequencing reads one may also look for "non-unique k-mers," defined as k-mers that occur more than once within a single read. Such k-mers are added to the graph, but only connected to the previous and next k-mer in the read. Thus, non-unique k-mers will not show up in any subsequent k-mer searches and cannot be connected to, avoiding formation of loops.

Additionally, when using a graph reference for the underlying reference alignment, information in the graph reference can also improve an assembly graph. For example, any k-mers or reads that fit the graph reference perfectly may be included in the assembly graph without checking base qualities, as it is highly unlikely that these reads have error. In particular, our results show that this significantly reduces the number of false negatives (FNs) in the resulting variant calls. A reduction in FNs is a significant result—while variations, any paths including variations with low support can be scored accordingly and discounted from further evaluation. In practice, each path through the graph is traversed and scored in this manner. The paths are then ranked, and a certain number (e.g., 128) of highest-scoring paths are submitted to a Pair-HMM algorithm to identify the most likely sequence for that sample (as described in further detail below). In this way, the Pair-HMM algorithm is only executed for a subset of the total number of paths in the assembly graph, improving the speed of the algorithm. Thus, high accuracy in scoring paths is desired.

Figure 6A:
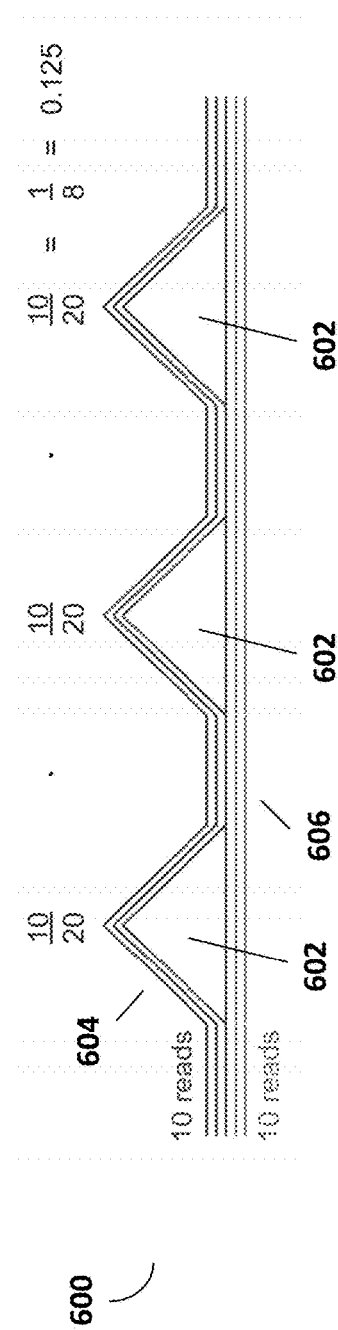
FIGS. 6A-B depict scoring schemes for a representative assembly graph according to the disclosure.

FIG. 6A illustrates a prior art method of scoring paths through an assembly graph. As shown in FIG. 6A, consider a graph 600 with three branching points 602, indicating differences at at least three different positions in the underlying sequence reads. Candidate sequences may be selected by assessing the number of reads that map to each branch site in order to determine the likelihood that any given variant should be included in a haplotype. As shown in FIG. 6A, 20 sequence reads are equally divided between two paths: a first path 604, and a second path 606 including the alternate variation at each branching point 602. Intuitively, each of these paths should have an equal score, e.g., 10 out of 20 reads, or 0.5, and any other paths should have a score of 0.

However, conventional methods of scoring paths fail to achieve this intuitive result. Conventional methods of scoring paths through assembly graphs score each variation site independently. In the example shown in FIG. 6A, each branching point 602 has an equal proportion of mapped reads (10 out of 20, or 0.5). To evaluate a path, these read count fractions may be multiplied together to generate a score, representing a likelihood of that sequence being present in the sample. In this case, the first path 604 and second path 606 each have a score of 0.125, representing a predicted likelihood of that path. However, any other path through the assembly graph (of which there are $2^3$, or 8) will have the same score. Thus, scoring paths in this manner only discounts variations with low read support, and may provide no actual improvement.

Evaluating Consistency Between Variant Sites

Figure 6B:
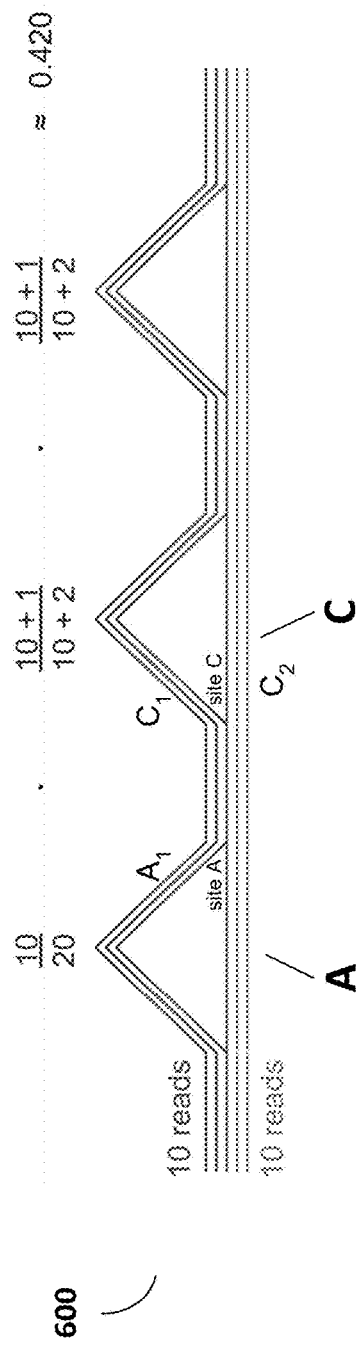

When scoring paths, methods according to the disclosure may consider variants in the context of the presence (or absence) of other variant sites. In the event that a given haplotype includes two nearby heterozygous variants (e.g., within a given read length), the inventor has recognized and appreciated that there should be a strong correlation between the two variants in the sequence data that can be used as information to determine the likelihood that either variant belongs in a given haplotype. As shown in FIG. 6B, variant sites 602 can instead be evaluated and scored in the context of a current path—i.e., the current haplotype or candidate sequence that is being considered that includes that variant. As shown in FIG. 6B, a first variant site A has no previous branch points and thus can be evaluated simply by read support.

If there are a significant number of reads that overlap two variant sites, one can generate a more accurate score for that candidate sequence that better estimates the likelihood of that candidate sequence being a "true" haplotype. In one embodiment, a score that considers consistency between variant sites within sequence reads considers set intersections. For example, for a haplotype that includes both variants A1 and C1 (the upward diverging paths at variant sites A and C, as shown in FIG. 6B), let $A_1$, $C_1$, and $C_2$ be the sets of reads that traverse the corresponding labelled branches in the graph, respectively. Then the score can be computed in terms of the cardinality (size) of set intersections, i.e.:

$$p = \frac{|A_1 \cap C_1| + 1}{|A_1 \cap C_1| + |A_1 \cap C_2| + 2}$$

This method predicts a likelihood of 0.42 for the haplotype that includes sites $A_1$, $B_1$, and $C_1$—a closer estimate to that present in the actual read data (10/20, or 0.5). By considering correlations between variants present in read data, this method distinguishes between variants of equal read support and presents a more accurate score that may be used to restrict the number of haplotypes for subsequent analysis and confirmation by, e.g., a Pair-HMM. Additionally, in some cases, one may even substitute this method for the Pair-HMM.

Evaluating consistency between variant sites when evaluating paths can significantly improve both the speed and quality of assembly-based variant calling. For example, candidate sequences can be quickly scored and "ranked" in order to identify a number of candidate haplotypes for subsequent confirmation by a PairHMM algorithm. Good results may be achieved by selecting fewer (e.g., 20) of the top haplotypes (from the $2^n$ possible haplotypes in a graph, where n is the number of variants in the graph) based on the computed score. This is a significant improvement over conventional methods which typically consider 128 or more different candidate sequences.

Optimizing Path Identification and Selection

As previously noted, typically every path in an assembly graph is enumerated, evaluated, and ranked before performing further processing. However, by evaluating read consistency across variant sites, graph traversal and path selection can be modified to calculate scores for fewer than all of the paths in the graph. In particular, as the graph is traversed to identify paths, at each variant site, outgoing paths with relatively higher scores (indicating a higher likelihood of that path being a "true" path) may be traversed first.

For purposes of the disclosure, a "path" comprises a sequence of connected nodes in the graph and a current score (e.g., a probability score) computed for that sequence. The current score can be the product of the scores for each of the variants in that path. A path can be a complete path (e.g., starting at the source node and ending at the sink node), or alternately be a partial path of fewer nodes.

Figure 7:
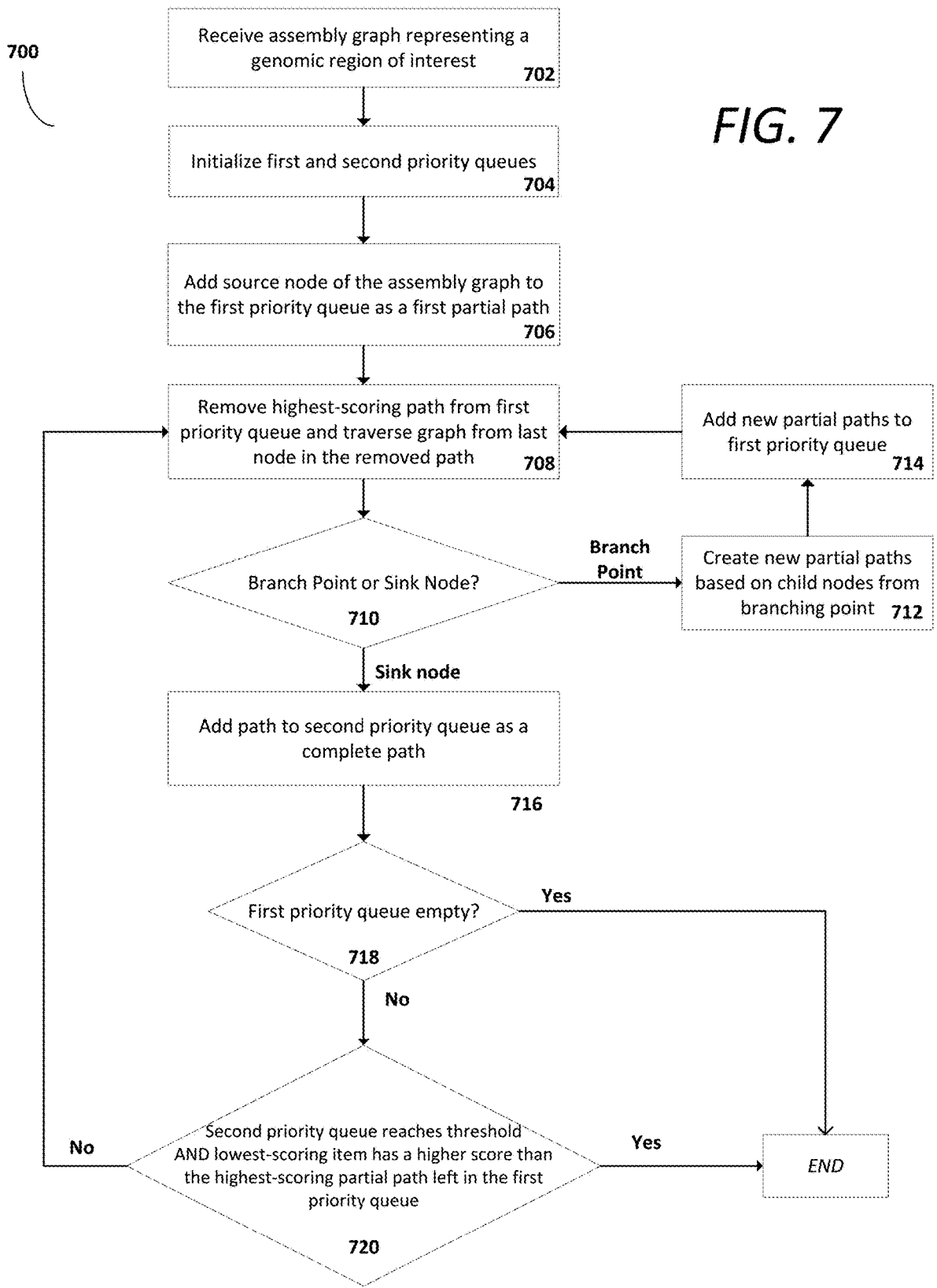
FIG. 7 is a flow diagram depicting an embodiment of a method for selecting candidate sequences from an assembly graph according to the disclosure.
Figure 8:
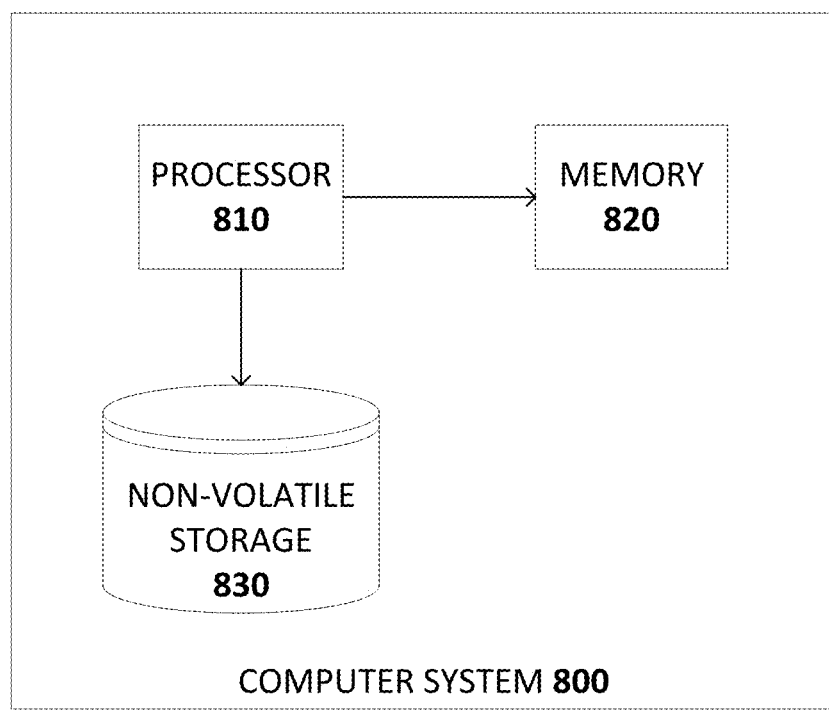
FIG. 8 is a block diagram of an illustrative computer system that may be used in implementing some embodiments of the technology described herein.

FIG. 7 depicts an exemplary method 700 of finding candidate paths through an assembly graph according to one embodiment of the disclosure. First, an assembly graph representing a genomic region of interest is received (step 702). Two priority queues are then initialized (step 704). As will be understood by one having skill in the art, a priority queue is a standard data structure that allows for the fast retrieval or removal of the highest-scoring (or lowest-scoring) item from a set of items. New items can be efficiently added to the priority queue, and will automatically assume their correct order. The first priority queue contains a set of partial paths through the assembly graph, wherein each path starts from the source node of the graph but ends before the sink node. The second priority queue contains a set of complete paths, wherein each path starts at the source node and ends at the sink node. Additionally, the second priority queue may be ordered inversely by score, such that the top result will be the lowest-scoring path.

To begin, the source node of the assembly graph is added to the first priority queue as a first partial path, and is assigned a score of 1 (step 706). The highest-scoring path from the priority queue is then removed, and the graph is traversed from the last node in the path (which, to start, will be the source node) (step 708). Graph traversal can comprise exploring successive child nodes from and appending child nodes to the partial path, until either a node is encountered that has two or more child nodes (i.e., a branching point), or a sink node is encountered (i.e., the end of the graph has been reached) (decision 710).

If the graph traversal arrives at a branching point (i.e., there are two or more child nodes available from the most recently encountered node), two or more partial paths are created corresponding to the current partial path and each of the two or more child nodes (step 712). The probability for each partial path is computed (e.g., by evaluating consistency between variant sites present in the sequence reads), and the new partial paths are then added back to the priority queue of partial paths (step 714).

However, if the graph traversal arrives at a sink node (or any node without a child node) then it has arrived at the end of the graph. In this case, the path is complete and its score is already computed. The complete path is added to the second priority queue as a complete path (step 716). If this causes the queue size to exceed a threshold number, i.e., the number of desired best-scoring paths, then we discard the lowest scoring path from the queue (as there is no point to keeping that path, because it would have no possibility of being in the overall top number). As previously noted, a typical threshold size is 20, though values between 8-50 work well.

This process continues until (a) the priority queue of partial paths is empty, indicating that we have explored all possible paths through the graph (decision 718); or (b) the priority queue of complete paths contains (e.g.) 20 items, and its lowest-scoring item has a higher score than the highest-scoring partial path left in the priority queue of partial paths, indicating that none of the remaining partial paths have any possibility of being in the top 20 (decision 720). By this process, we focus on only the most promising paths, and avoid exploring many low-probability paths, significantly reducing the number of calculations required to evaluate candidate sequences.

Because the most probable candidate sequences are the first to be enumerated, there is no need to explore all possible paths—low-probability paths can be ignored. Paths are enumerated until a threshold of candidate sequences is reached. Various threshold values may be used; for example, a range of 8-50 may provide good results, and a default threshold of 20 will generally work for most applications.

determines the likelihood that each sequence read within the reassembly window was generated from the candidate sequence. By aggregating these likelihoods, one can select those candidate variants from candidate sequences that are best supported by the sequence reads.

III. Exemplary Results

Tables II and III below illustrate a comparison of results using an "old" method (i.e., variant sites are considered independently) vs. a "new" method that considers conditional probability, such as a method that considers read consistency and computes only a sufficient number of paths according to the disclosure. The old method is used to select either 20 candidate haplotypes (for direct comparison with the new method) or 128 candidate haplotypes, which is the default of the old method and requires the longest runtime.

In Table II, below, processing speed is fastest using the new method, as compared to the old method when selecting 20 haplotypes or the default 128 haplotypes. Additionally, the new method demonstrates an improvement for all variants with respect to precision, recall, and F-score as compared to the old method with 128 candidate haplotypes.

TABLE II

| Haplotype selection method | Max haplotypes | Runtime on c4.2xlarge (hh:mm) | All variants | | | SNP | | | INDEL | | |
|---|---|---|---|---|---|---|---|---|---|---|---|
| | | | Precision | Recall | F-score | Precision | Recall | F-Score | Precision | Recall | F-score |
| Old | 20 | 8:01 | 99.7750 | 99.8636 | 99.8193 | 99.8214 | 99.9303 | 99.8758 | 99.3646 | 99.2761 | 99.3203 |
| Old | 128 | 10:10 | 99.7698 | 99.8855 | 99.8276 | 99.8152 | 99.9519 | 99.8835 | 99.3678 | 99.3009 | 99.3344 |
| New | 20 | 7:54 | 99.7717 | 99.8859 | 99.8288 | 99.8174 | 99.9523 | 99.8848 | 99.3670 | 99.3012 | 99.3341 |

This is in contrast to traditional methods that default to a selection of 128 candidate sequences to pass on to the following step (i.e., using Hidden Markov Models (HMMs) to evaluate the sequences), which is very computationally expensive.

In Table III, below, the new method captures more true positives (TP) for all variants as compared to the old method using 20 candidate haplotypes, and also generates a marked reduction in false negatives (FN), thus providing both qualitative and quantitative improvements.

TABLE III

| Haplotype selection method | Max haplotypes | Runtime on c4.2xlarge (hh:mm) | All variants | | | SNP | | | INDEL | | |
|---|---|---|---|---|---|---|---|---|---|---|---|
| | | | TP | FP | FN | TP | FP | FN | TP | FP | FN |
| Old | 20 | 8:01 | 3,506,406 | 7,906 | 4,791 | 3,151,743 | 5,638 | 2,198 | 354,663 | 2,268 | 2,593 |
| Old | 128 | 10:10 | 3,507,173 | 8,093 | 4,020 | 3,152,421 | 5,836 | 1,516 | 354,752 | 2,257 | 2,504 |
| New | 20 | 7:54 | 3,507,166 | 8,026 | 4,006 | 3,152,414 | 5,766 | 1,503 | 354,752 | 2,260 | 2,503 |

Assign Sample Genotypes Based on the Highest Scoring Candidate Sequences

Once a set of candidate sequences are scored and ranked, they can be compared to the reference sequence in order to identify variation. For example, the Smith-Waterman algorithm or the Needleman-Wunsch algorithm can be used to map each haplotype in turn to the reference sequence within the reassembly window, yielding a CIGAR string describing any differences between the reference sequence and the candidate sequence identified from local assembly. These differences are candidate variants, which may be further evaluated (e.g., by a Pair-HMM as taught by Richard Durbin in the text "Biological Sequence Analysis: Probabilistic Models of Proteins and Nucleic Acids". The Pair-HMM IV. Computer Systems An illustrative implementation of a computer system 800 that may be used in connection with any of the embodiments of the disclosure provided herein is shown in FIG. 10. The computer system 800 may include one or more processors 810 and one or more articles of manufacture that comprise non-transitory computer-readable storage media (e.g., memory 820 and one or more non-volatile storage media 830). The processor 810 may control writing data to and reading data from the memory 820 and the non-volatile storage device 830 in any suitable manner, as the aspects of the disclosure provided herein are not limited in this respect. To perform any of the functionality described herein, the processor 810 may execute one or more processor-executable instructions stored in one or more non-transitory computer-readable storage media (e.g., the memory 820), which may serve as non-transitory computer-readable storage media storing processor-executable instructions for execution by the processor 810.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided including with reference to FIG. 5. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

What is claimed is:

1. A system for identifying variation in a genomic sample relative to a human reference genome, the system comprising:

at least one computer hardware processor; and at least one non-transitory computer-readable storage medium storing processor-executable instructions that, when executed by the at least one computer hardware processor, cause the at least one computer hardware processor to perform:

accessing, from the at least one non-transitory computer-readable storage medium, a set of sequence reads stored in an electronic format;

aligning the set of sequence reads from the genomic sample against the human reference genome to obtain an alignment indicating a mapping of the set of sequence reads to respective regions of the human reference genome;

selecting, using the mapping indicated by the alignment and from among the set of sequence reads, a plurality of sequence reads mapping to a genomic region of interest in the human reference genome and containing variation relative to the genomic region of interest in the human reference genome;

generating at least one data structure embodying a directed acyclic graph (DAG) by assembling the DAG from the plurality of sequence reads, the DAG comprising a plurality of nodes and edges representing relationships among nodes in the plurality of nodes, at least some of the nodes representing respective branch sites representing variation present in the plurality of sequence reads, each branch site of the respective branch sites comprising two or more branches, wherein:

a plurality of paths through the DAG represents a respective plurality of candidate sequences; and a first path of the plurality of paths through the DAG comprises a set of successive branches over two or more branch sites and represents a first candidate sequence of the plurality of candidate sequences;

selecting, using the at least one data structure embodying the DAG, a subset of the plurality of candidate sequences represented by the plurality of paths through the DAG, the subset of candidate sequences including the first candidate sequence, the selecting comprising:

determining a number of the plurality of sequence reads that span the successive branches over the two or more branch sites; and selecting, from the plurality of candidate sequences and using the number of the plurality of sequence reads that span the successive branches over the two or more branch sites and multiple priority queue data structures including a first priority queue and a second priority queue, the first candidate sequence for inclusion into the subset of candidate sequences, the selecting comprising:

using the first priority queue and the second priority queue to identify the first candidate sequence for inclusion into the subset of candidate sequences at least in part by using the first priority queue to manage partial paths through the DAG and the second priority queue to manage complete paths through the DAG; and identifying the variation in the genomic sample by identifying at least one variant using the selected subset of candidate sequences, the identifying comprising:

aligning the selected subset of the plurality of candidate sequences against the human reference genome; and identifying the at least one variant using results of the aligning.

2. The system of claim 1, wherein the selecting further comprises:
calculating a ratio of: the number of sequence reads that align to both a first branch of a first branch site and a first branch of a second branch site, over the number of sequence reads that align to both the first branch of the first branch site and the first branch of the second branch site, and the number of sequence reads that align to both the first branch of the first branch site and a second branch of the second branch site.

3. The system of claim 1, wherein the selecting further comprises selecting multiple ones of the plurality of candidate sequences for inclusion into the subset of candidate sequences.

4. The system of claim 1, wherein the selecting the subset of candidate sequences further comprises:
traversing the DAG and identifying one or more partial paths, each partial path comprising one or more nodes;
selecting partial paths with highest read support for continued traversal to identify one or more completed paths;
storing a threshold number of the one or more completed paths using the first priority queue; and
selecting at least one completed path as a candidate sequence once the identified one or more partial paths have less read support than the threshold number of the one or more completed paths.

5. The system of claim 1, wherein the set of sequence reads is stored in a FASTA or a FASTQ electronic format.

6. The system of claim 1, wherein the selecting further comprises identifying the genomic region of interest using a first pointer and a second pointer, wherein the first pointer indicates a variant window and the second pointer indicates an assembly window.

7. A method of identifying variation in a genomic sample relative to a human reference genome, the method comprising using at least one computer hardware processor to perform:
accessing, from at least one non-transitory computer-readable storage medium, a set of sequence reads stored in an electronic format;
aligning the set of sequence reads from the genomic sample against the human reference genome to obtain an alignment indicating a mapping of the set of sequence reads to respective regions of the human reference genome;
selecting, using the mapping indicated by the alignment and from among the set of sequence reads, a plurality of sequence reads mapping to a genomic region of interest in the human reference genome and containing variation relative to the genomic region of interest in the human reference genome;
generating at least one data structure embodying a directed acyclic graph (DAG) by assembling the DAG from the plurality of sequence reads the DAG comprising a plurality of nodes and edges representing relationships among nodes in the plurality of nodes, at least some of the nodes representing respective branch sites representing variation present in the plurality of sequence reads, each branch site of the respective branch sites comprising two or more branches, wherein:
a plurality of paths through the DAG represent a respective plurality of candidate sequences; and
a first path of the plurality of paths through the DAG comprises a set of successive branches over two or more branch sites and represents a first candidate sequence of the plurality of candidate sequences;
selecting, using the at least one data structure embodying the DAG, a subset of the plurality of candidate sequences represented by the plurality of paths through the DAG, the subset of candidate sequences including the first sequence, the selecting comprising:
determining a number of the plurality of sequence reads that span the successive branches over the two or more branch sites; and
selecting, from the plurality of candidate sequences and using the number of the plurality of sequence reads that span the successive branches over the two or more branch sites and multiple priority queue data structures including a first priority queue and a second priority queue, the first candidate sequence for inclusion into the subset of candidate sequences, the selecting comprising:
using the first priority queue and the second priority queue to identify the first candidate sequence for inclusion into the subset of candidate sequences at least in part by using the first priority queue to manage partial paths through the DAG and the second priority queue to manage complete paths through the DAG; and
identifying the variation in the genomic sample by identifying at least one variant using the selected set of candidate sequences, the identifying comprising:
aligning the selected subset of the plurality of candidate sequences against the human reference genome; and
identifying the at least one variant using results of the aligning.

8. The method of claim 7, wherein the set of sequence reads is stored in a FASTA or a FASTQ electronic format.

9. The method of claim 7, wherein the selecting further comprises identifying the genomic region of interest using a first pointer and a second pointer, wherein the first pointer indicates a variant window and the second pointer indicates an assembly window.

10. The method of claim 7, wherein the selecting further comprises:
calculating a ratio of: the number of sequence reads that align to both a first branch of a first branch site and a first branch of a second branch site, over the number of sequence reads that align to both the first branch of the first branch site and the first branch of the second branch site, and the number of sequence reads that align to both the first branch of the first branch site and a second branch of the second branch site.

11. The method of claim 7, wherein the selecting the subset of candidate sequences further comprises:
traversing the DAG and identifying one or more partial paths, each partial path comprising one or more nodes;
selecting partial paths with highest read support for continued traversal to identify one or more completed paths;
storing a threshold number of the one or more completed paths using the first priority queue; and
selecting at least one completed path as a candidate sequence once the identified one or more partial paths have less read support than the threshold number of the one or more completed paths.

12. The method of claim 7, wherein the selecting further comprises selecting multiple ones of the plurality of candidate sequences for inclusion into the subset of candidate sequences.

13. At least one non-transitory computer-readable storage medium storing processor executable instructions that, when executed by at least one computer hardware processor, cause the at least one computer hardware processor to perform:
- accessing, from the at least one non-transitory computer-readable storage medium, a set of sequence reads stored in an electronic format;
- aligning the set of sequence reads from a genomic sample against a human reference genome to obtain an alignment indicating a mapping of the set of sequence reads to respective regions of the human reference genome;
- selecting, using the mapping indicated by the alignment and from among the set of sequence reads, a plurality of sequence reads mapping to a genomic region of interest in the human reference genome and containing variation relative to the genomic region of interest in the human reference genome;
- generating at least one data structure embodying a directed acyclic graph (DAG) by assembling the DAG from the plurality of sequence reads the DAG comprising a plurality of nodes and edges representing relationships among nodes in the plurality of nodes, at least some of the nodes representing respective branch sites representing variation present in the plurality of sequence reads, each branch site of the respective branch sites comprising two or more branches, wherein:
  - a plurality of paths through the DAG represent a respective plurality of candidate sequences; and
  - a first path of the plurality of paths through the DAG comprises a set of successive branches over two or more branch sites and represents a first candidate sequence of the plurality of candidate sequences;
- selecting, using the at least one data structure embodying the DAG, a subset of the plurality of candidate sequences represented by the plurality of paths through the DAG, the subset of candidate sequences including the first sequence, the selecting comprising:
  - determining a number of the plurality of sequence reads that span the successive branches over the two or more branch sites; and
  - selecting, from the plurality of candidate sequences and using the number of the plurality of sequence reads that span the successive branches over the two or more branch sites and multiple priority queue data structures including a first priority queue and a second priority queue, the first candidate sequence for inclusion into the subset of candidate sequences, the selecting comprising:
    - using the first priority queue and the second priority queue to identify the first candidate sequence for inclusion into the subset of candidate sequences at least in part by using the first priority queue to manage partial paths through the DAG and the second priority queue to manage complete paths through the DAG; and
- identifying the variation in the genomic sample by identifying at least one variant using the selected set of candidate sequences, the identifying comprising:
  - aligning the selected subset of the plurality of candidate sequences against the human reference genome; and
  - identifying the at least one variant using results of the aligning.

14. The at least one non-transitory computer-readable storage medium of claim 13, wherein the set of sequence reads is stored in a FASTA or a FASTQ electronic format.

15. The at least one non-transitory computer-readable storage medium of claim 13, wherein the selecting further comprises identifying the genomic region of interest using a first pointer and a second pointer, wherein the first pointer indicates a variant window and the second pointer indicates an assembly window.

16. The at least one non-transitory computer-readable storage medium of claim 13, wherein the selecting further comprises:
- calculating a ratio of: the number of sequence reads that align to both a first branch of a first branch site and a first branch of a second branch site, over the number of sequence reads that align to both the first branch of the first branch site and the first branch of the second branch site, and the number of sequence reads that align to both the first branch of the first branch site and a second branch of the second branch site.

17. The at least one non-transitory computer-readable storage medium of claim 13, wherein the selecting the subset of candidate sequences further comprises:
- traversing the DAG and identifying one or more partial paths, each partial path comprising one or more nodes;
- selecting partial paths with highest read support for continued traversal to identify one or more completed paths;
- storing a threshold number of the one or more completed paths; and
- selecting at least one completed path as a candidate sequence once the identified one or more partial paths have less read support than the threshold number of the one or more completed paths.

* * * * *